United States Patent
Wilson et al.

(10) Patent No.: US 9,678,024 B1
(45) Date of Patent: Jun. 13, 2017

(54) METHODS AND SYSTEMS FOR NON-INTRUSIVE CHEMICAL ASSAYING OF HYDROGENOUS MATERIALS AND MIXTURES USING COMBINED NEUTRON ACTIVATION AND NUCLEAR RESONANCE FLUORESCENCE

(71) Applicant: Passport Systems, Inc., Billerica, MA (US)

(72) Inventors: Cody M. Wilson, Watertown, MA (US); William Bertozzi, Lexington, MA (US); Daniel L. Higgs, Weymouth, MA (US); Stephen E. Korbly, Acton, MA (US); Robert J. Ledoux, Harvard, MA (US)

(73) Assignee: Passport Systems, Inc., Billerica, MA (US)

( * ) Notice: Subject to any disclaimer, the term of this patent is extended or adjusted under 35 U.S.C. 154(b) by 0 days.

(21) Appl. No.: 15/094,490

(22) Filed: Apr. 8, 2016

(51) Int. Cl.
   *G01N 23/221* (2006.01)
   *G01N 23/222* (2006.01)
   *G01N 23/223* (2006.01)
   *G01N 23/22* (2006.01)

(52) U.S. Cl.
   CPC ....... *G01N 23/2208* (2013.01); *G01N 23/223* (2013.01)

(58) Field of Classification Search
   CPC ... G01N 23/221; G01N 23/222; G01N 23/223
   USPC .............. 436/35, 110–111, 127, 144; 378/88
   See application file for complete search history.

(56) References Cited

U.S. PATENT DOCUMENTS

| | | | | |
|---|---|---|---|---|
| 4,209,695 A * | 6/1980 | Arnold | ................. | G01N 23/222 250/261 |
| 4,251,726 A * | 2/1981 | Alvarez | ............... | G01N 23/221 102/200 |
| 4,314,155 A * | 2/1982 | Sowerby | .......... | G01N 23/20083 250/253 |
| 4,941,162 A * | 7/1990 | Vartsky | ................ | G01N 23/066 378/3 |
| 5,040,200 A * | 8/1991 | Ettinger | ............... | G01V 5/0025 378/3 |
| 5,115,459 A | 5/1992 | Bertozzi | | |
| 5,293,414 A * | 3/1994 | Ettinger | ............... | G01V 5/0025 376/157 |

(Continued)

OTHER PUBLICATIONS

Buffler, A., Radiation Physics and Chemistry 2004, 71, 853-861.*

(Continued)

*Primary Examiner* — Arlen Soderquist
(74) *Attorney, Agent, or Firm* — Foley Hoag LLP; Rajesh Vallabh

(57) ABSTRACT

Methods and systems are disclosed wherein neutrons are produced by a photon induced process 2D(γ,n) and the ensuing neutrons are thermalized and captured by hydrogen producing a 2.223 MeV gamma that is used to identify and quantify the presence of hydrogen and which, when combined with NRF signals from certain isotopes, can be used to establish the nature of a hydrogenous compound or a mixture of hydrogenous materials or a mixture of hydrogenous materials with other non-hydrogenous materials. The method is useful to establish, e.g., the presence and quantification of explosives, toxic substances and general contraband as well as the flow of materials in a production line or shipping venue.

31 Claims, 4 Drawing Sheets

(56) References Cited

U.S. PATENT DOCUMENTS

| | | | | |
|---|---|---|---|---|
| 5,420,905 | A * | 5/1995 | Bertozzi | G01N 23/20091 378/86 |
| 6,393,085 | B1 * | 5/2002 | Heller | G01N 23/025 376/157 |
| 6,791,089 | B1 * | 9/2004 | Caffrey | G01N 23/222 250/358.1 |
| 7,214,942 | B2 * | 5/2007 | Gardner | G01V 5/125 250/360.1 |
| 7,372,262 | B2 | 5/2008 | Bertozzi et al. | |
| 7,486,769 | B2 * | 2/2009 | Brondo, Jr. | G01V 5/0069 378/57 |
| 9,170,218 | B2 * | 10/2015 | Naqvi | G01N 23/222 |
| 2004/0256566 | A1 * | 12/2004 | Gardner | G01V 5/125 250/360.1 |
| 2006/0188060 | A1 * | 8/2006 | Bertozzi | G01N 23/20066 378/57 |
| 2006/0193433 | A1 * | 8/2006 | Ledoux | G01N 23/223 378/57 |
| 2007/0019788 | A1 * | 1/2007 | Ledoux | G01N 23/04 378/88 |
| 2007/0263767 | A1 * | 11/2007 | Brondo | G01V 5/0069 378/57 |
| 2011/0064200 | A1 | 3/2011 | Bertozzi et al. | |
| 2015/0168319 | A1 * | 6/2015 | Naqvi | G01N 23/222 250/393 |

OTHER PUBLICATIONS

Farrell, J. P. et al, SPIE 2005, 5769, 1-10.*
Runkle, R. C. et al, Nuclear Instruments and Methods in Physics Research A 2009, 603, 510-528.*
Litz, M. et al, ARL-TR-5871 2012, 48 pages.*

* cited by examiner

METHODS AND SYSTEMS FOR NON-INTRUSIVE CHEMICAL ASSAYING OF HYDROGENOUS MATERIALS AND MIXTURES USING COMBINED NEUTRON ACTIVATION AND NUCLEAR RESONANCE FLUORESCENCE

STATEMENT AS TO FEDERALLY SPONSORED RESEARCH

This invention was made with Government support under contract number HSHQDC-12-C-00059 awarded to Passport Systems, Inc. by The United States Department of Homeland Security/Domestic Nuclear Detection Office. The Government may have certain rights in the invention.

BACKGROUND

The present application generally relates to methods and systems for the non-intrusive determination of the chemistry of materials and mixtures. More particularly, the application relates to chemical assaying of hydrogenous materials and mixtures using combined neutron activation and nuclear resonance fluorescence.

The ability to determine the chemistry of bulk materials in a stand-off, non-destructive manner is valuable to many security and commercial operations in a global scenario. For instance, in the US, security operations such as Customs and Border Protection (CBP) and the Transportation Security Association (TSA) have a core mission to determine the presence of contraband in concealed containers. Additionally, commercial operations have interests for material tracking including applications such as supply chain control. Techniques for the detection and quantification of specified materials are valuable to these missions on a global basis.

Nuclear resonance fluorescence (NRF) (disclosed, e.g., in U.S. Pat. Nos. 5,420,905 and 5,115,459) is an established technique for the non-destructive determination of the presence of individual isotopes. Similarly, neutron capture by hydrogen provides a well-known gamma signal for its presence. However, many real-life situations do not allow the use of neutron beams to provide information concerning the hydrogenous content of a specific position in a container. This is generally due to attenuation of neutron beams by thick hydrogenous materials such as water or wood or other materials.

In chemical assaying techniques disclosed herein, the neutrons are generated within the sample itself, very near or at the location of interest within the container. Only the transmission of a photon beam is needed to reach a specific location, not the neutrons from an external beam. The techniques disclosed herein involve a novel method for neutron production and a fusion of the neutron capture signal with the signals from NRF. The result is a novel technique wherein during one common exposure by a photon beam, it is possible to discover and measure for a specific location in a container: (a) the hydrogenous nature of the material through neutron production from $2D(\gamma,n)$ and capture by hydrogen, (b) the presence of other nuclear species via the complimentary use of NRF, and (c) the nature of the hydrogenous chemical element or admixtures that are present in a specific location via the fusion of these data from (a) and (b).

BRIEF SUMMARY OF THE DISCLOSURE

In accordance with one or more embodiments, a non-intrusive method is provided for analyzing the chemical makeup of a target hydrogenous material sample in a voxel. The method comprises the steps of: (a) illuminating the target hydrogenous material sample in the voxel with a photon beam, wherein the energy of at least some photons in the photon beam is greater than 2.23 MeV; (b) measuring a first number of 2.223 MeV photons produced by neutron capture and emitted from the target hydrogenous material sample in the voxel in a given measurement direction in a first energy range that contains the energy corresponding to neutron capture by hydrogen; (c) measuring a second number of Nuclear Resonance Fluorescence (NRF) produced photons emitted from the target hydrogenous material sample in the voxel in the given measurement direction in a second energy range; (d) determining the intensity of the 2.223 MeV photons produced by neutron capture in the target hydrogenous material sample in the voxel; (e) determining which isotopes are present in the target hydrogenous material sample in the voxel based on the second number of NRF produced photons; (f) determining the intensities of the NRF produced photons; (g) determining the ratio of the abundances of the isotopes in the voxel from the intensities of the of the NRF produced photons; (h) determining the ratios of the hydrogen content in the voxel to the content of the isotopes of the target hydrogenous material sample in the voxel; and (i) determining the elemental composition of the target hydrogenous material sample in the voxel.

In accordance with one or more further embodiments, a non-intrusive system is provided for analyzing the chemical makeup of a target hydrogenous material sample in a voxel. The system includes a photon source for illuminating the target hydrogenous material sample in the voxel with a photon beam, wherein the energy of at least some photons in the photon beam is greater than 2.23 MeV. The system also includes a detector for (a) detecting a first number of 2.223 MeV photons produced by neutron capture and emitted from the target hydrogenous material sample in the voxel in a given measurement direction in a first energy range that contains the energy corresponding to neutron capture by hydrogen, and (b) detecting a second number of Nuclear Resonance Fluorescence (NRF) produced photons emitted from the target hydrogenous material sample the voxel in the given measurement direction in a second energy range. The system further includes a computer system, comprising: at least one processor; memory associated with the at least one processor; and a program supported in the memory. The program contains a plurality of instructions which, when executed by the at least one processor, cause the at least one processor, in response to data received from the detector, to: (a) determine the intensity of the 2.223 MeV photons produced by neutron capture in the target hydrogenous material sample the voxel; (b) determine which isotopes are present in the target hydrogenous material sample in the voxel based on the second number of NRF produced photons; (c) determine the intensities of the NRF produced photons; (d) determine the ratio of the abundances of the isotopes in the voxel from the intensities of the of the NRF produced photons; (e) determine the ratios of the hydrogen content in the voxel to the content of the isotopes of the target hydrogenous material sample in the voxel; and (f) determine the elemental composition of the target hydrogenous material sample in the voxel.

DETAILED DESCRIPTION

Various embodiments disclosed herein are directed to methods and systems for the non-intrusive determination of the chemistry of hydrogenous materials. A method in accordance with one or more embodiments determines the composition of a hydrogenous material via:

(a) Production of neutrons in hydrogen using a gamma ray source with energy exceeding the (γ,n) threshold of deuterium (2.223 MeV). Subsequently, the detection of characteristic gamma rays resulting from neutron capture by hydrogen in the material. This data informs as to the presence of hydrogen and the amount. Deuterium is a naturally occurring isotope of hydrogen at the level of approximately 0.015% by population. Since it is co-spatial with normal hydrogen, the production of neutrons by (γ,n) on deuterium and their thermalization and capture by normal hydrogen is very efficient.

(b) Excitation of various nuclear resonance states in a wide variety of isotopes representing many common elements using a bremsstrahlung photon beam. Subsequently, the detection of the characteristic gamma rays resulting from de-excitation of these states: Nuclear Resonance Fluorescence (NRF). This data identifies the elements that are part of the hydrogenous chemical or mixture and their amounts.

(c) Fusion of the data from (a) and (b) to determine the chemical makeup of the hydrogenous material and/or admixtures comprising the hydrogenous material. Fusion of the data from (a) and (b) allows a determination of the relative elemental abundance of the hydrogenous chemical materials or mixtures in the various regions of interest of the sample or container being examined.

In accordance with one or more embodiments, the system utilizes a photon beam having energies that on the one hand overlap with the NRF states of the elements of interest and on the other hand are greater than 2.223 MeV and are able to produce neutrons from the naturally occurring deuterium in hydrogen within the interrogated sample. Using NRF requires photons able to excite the states at 7.1169 MeV and/or at 6.9171 MeV in oxygen. These are the highest energy NRF states that are of practical consequence. A bremsstrahlung beam with a 9 MeV end-point comfortably covers all possibilities. However, lower bremsstrahlung energies can be used to detect hydrogen and to detect other nuclear species using NRF. Those skilled in the art will recognize the different possibilities and objectives that allow for different bremsstrahlung endpoint energies and/or monochromatic photon energies and these are included herein as obvious extensions of this patent.

Figure 1:
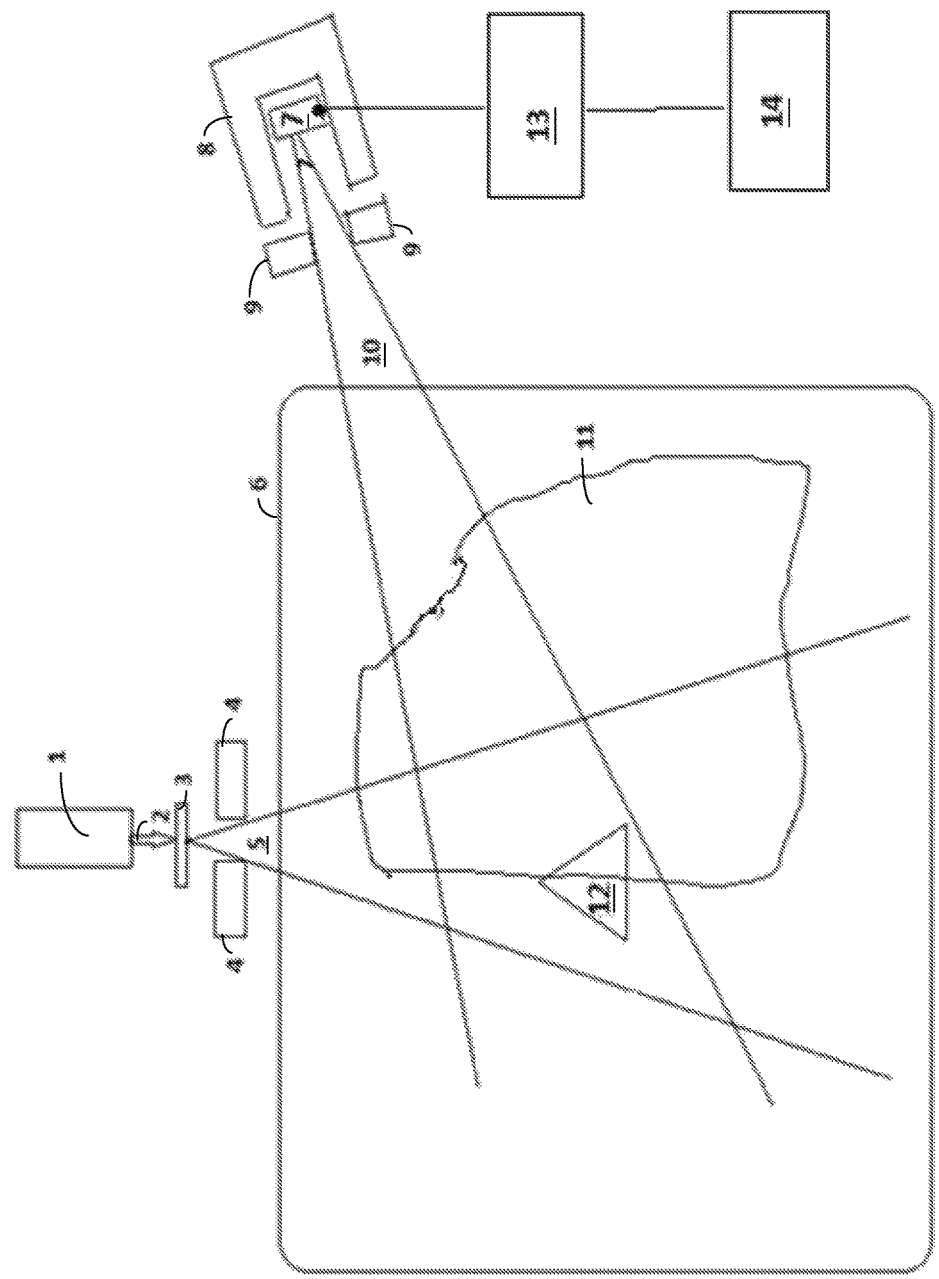
FIG. 1 is a schematic diagram illustrating an exemplary system for the non-intrusive determination of the chemistry of materials and mixtures in accordance with one or more embodiments.

FIG. 1 is a simplified diagram illustrating an exemplary system for the non-intrusive determination of the chemistry of materials and mixtures in accordance with one or more embodiments. An electron accelerator 1 produces an energetic beam of electrons 2 incident on a target 3 from which a beam of bremsstrahlung 5 is radiated and collimated at 4. The collimated bremsstrahlung beam 5 is incident upon and passes through a container 6. Within the container 6, the collimated bremsstrahlung beam 5 interacts with different materials along its path.

The material in the container is also viewed by a spectroscopic x-ray detector 7 that is shielded by an enclosure 8. Part of the detector shield 8 serves to collimate at 9 the detector view 10. Signals from the detector are accumulated and treated by an acquisition system 13 and fed to a computer 14 for analysis. This analysis utilizes algorithms to determine the composition of materials in each voxel viewed by the detectors and presents the results in various forms appropriate for specific operating concepts to alert operators or preset programs as to the elements and chemicals present in the voxel of interest. The intersection of the collimated photon beam 5 and the collimated view 10 of the detector defines the primary voxel of interest or simply the "voxel."

Those skilled in the art will recognize the various forms of analysis and presentation appropriate for the large variety of possible requirements by those using this information and these are all included herein as obvious extensions of this patent. In this exemplary arrangement the collimated bremsstrahlung beam 5 interacts with hydrogenous material 11 and other materials 12. The detector 7 views the hydrogenous material 11 and an unspecified material 12, both of which are in the bremsstrahlung beam 5. The detector 7 (in another position or a second detector in an appropriate position, not shown in the figure) also views the unspecified material 12, which is in the bremsstrahlung beam, and possibly inside the hydrogenous material or not inside the hydrogenous material. The intersection of the collimated bremsstrahlung beam 5 with the detector collimated field of view 10 forms the measurement voxel. In this exemplary arrangement, the main signals originate from the hydrogenous material 11 and the possibly-hydrogenous material 12, both of which are viewed by the detector 7 with collimated view 10 and irradiated by the collimated photon beam 5. Neutrons are produced by the hydrogenous material, thermalized, and captured by the hydrogen therein producing the 2.223 MeV photon signal. The existence of other isotopes in the hydrogenous material is provided by the NRF signals from the primary voxel. The relative sizes of these signals provide the data that establishes the ratio of isotopes forming the hydrogenous material or mixture within the primary voxel. The relative chemical makeup of the hydrogenous material or mixture follows from this ratio with the use of given algorithms.

Figure 2:
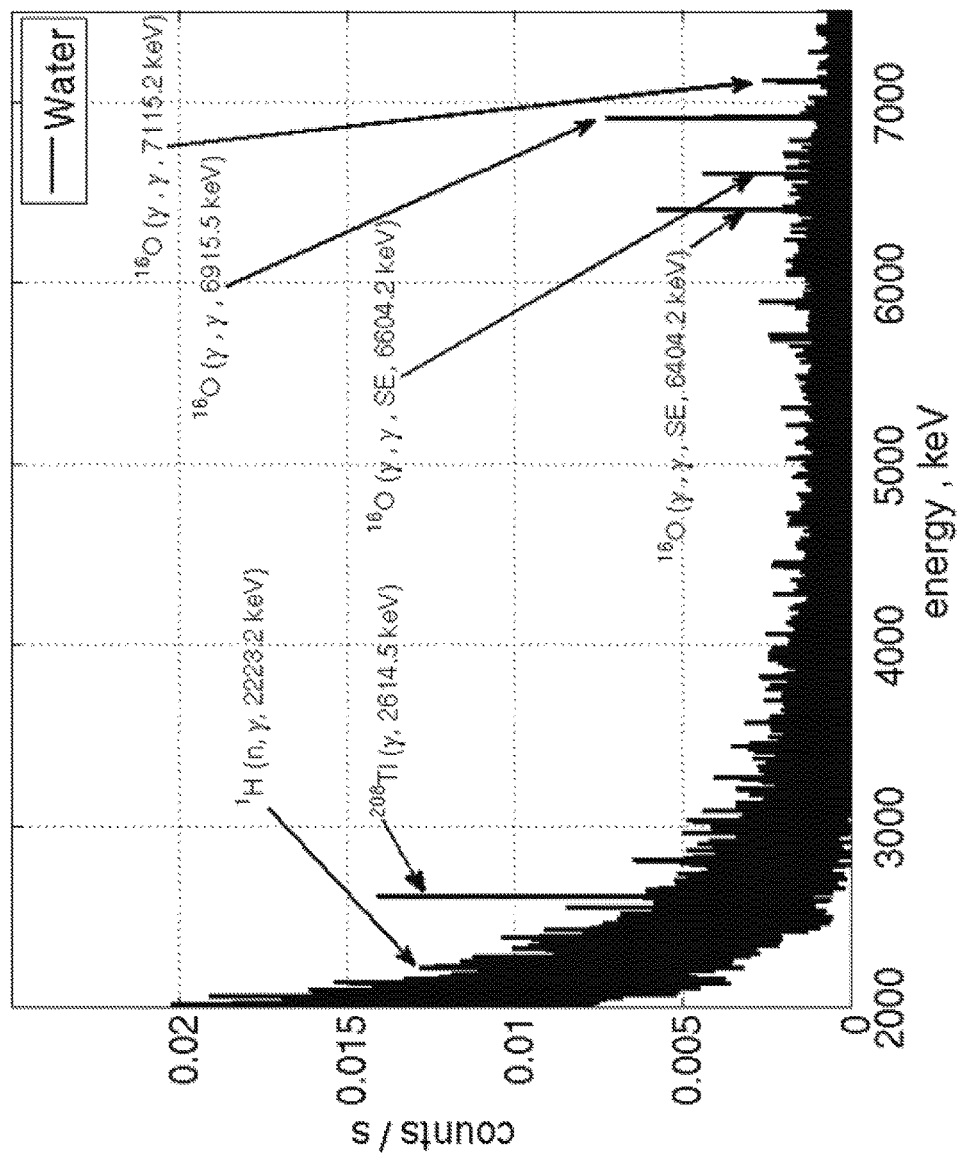
FIG. 2 is a graph illustrating the photon spectrum of water determined by the system of FIG. 1.
Figure 3:
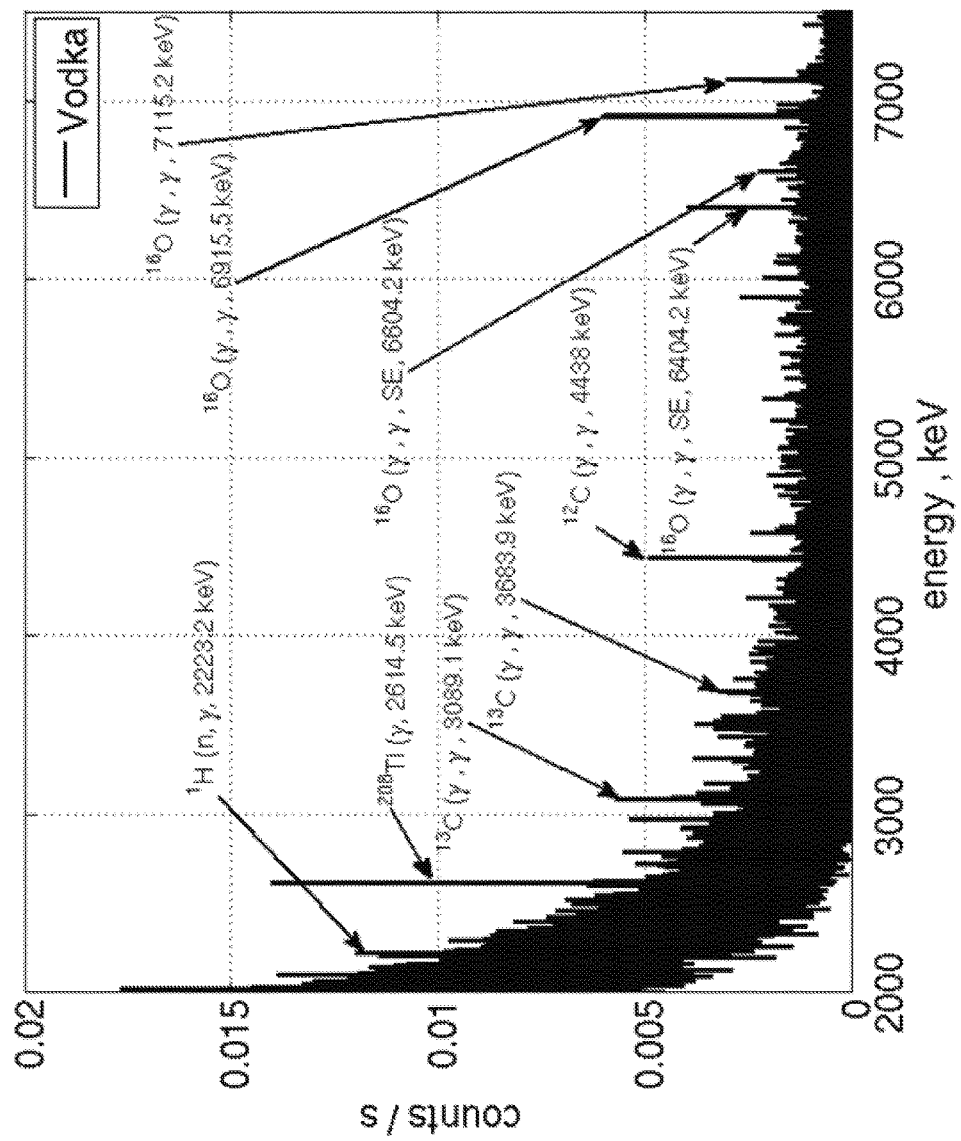
FIG. 3 is a graph illustrating the photon spectrum of mixture of alcohol and water (Vodka) determined by the system of FIG. 1.
Figure 4:
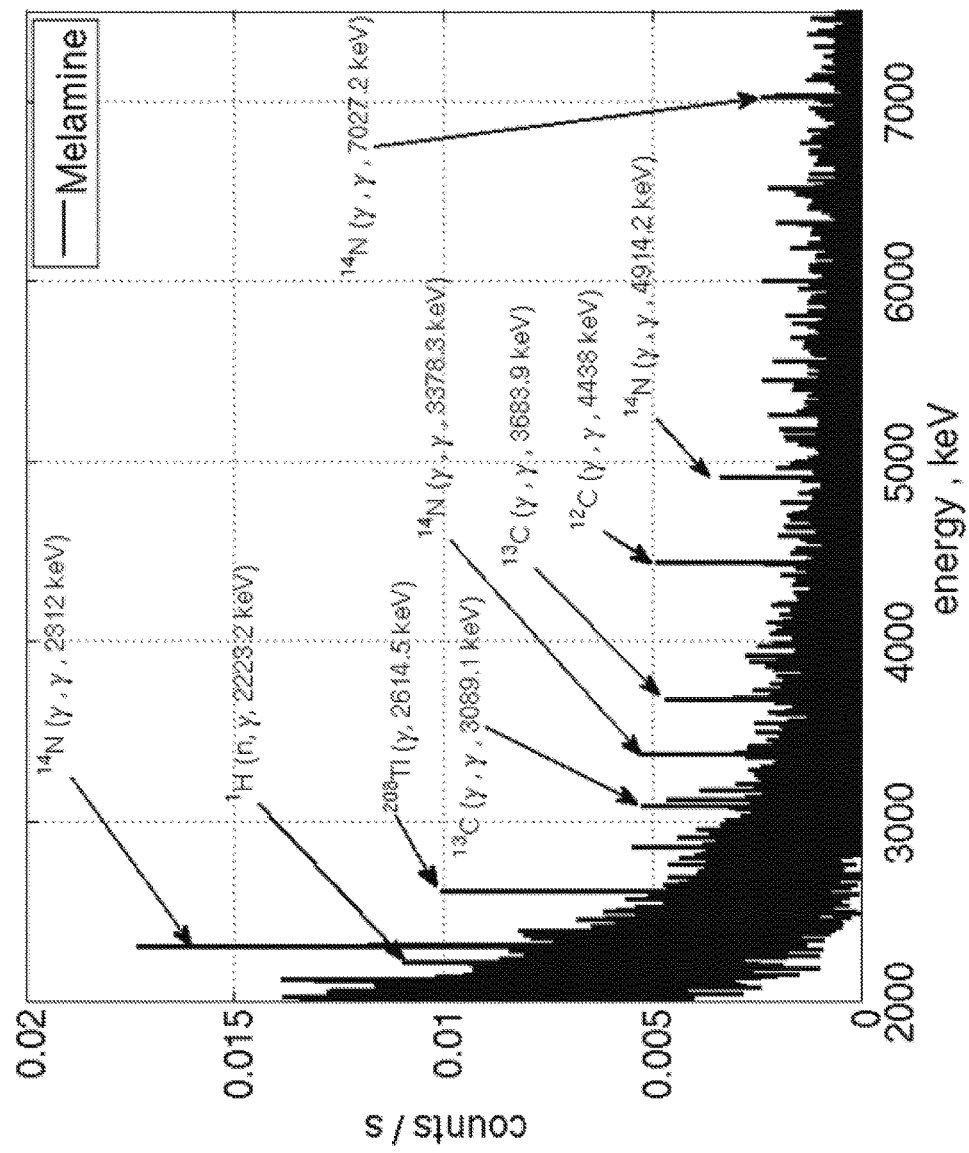
FIG. 4 is a graph illustrating the photon spectrum of melamine determined by the system of FIG. 1.

The existence of hydrogenous material is determined by the observation of the 2.223 MeV photons. This signal establishes that hydrogenous material is present in the primary voxel because of its unique origin given the experimental circumstances. The amount of hydrogen in a specific region will be determined by: the intensity of the 2.223 MeV line; the flux of the photon beam; the scattering cross section for (n,p) scattering which thermalizes the neutrons; and the cross section for neutron capture by the hydrogen protons resulting in the production of deuterium and the 2.223 MeV photon. FIGS. 2, 3, and 4 show photon spectra viewed by the collimated detector 7 for three different hydrogenous targets irradiated with 9 MeV bremsstrahlung in an exemplary arrangement similar to that in FIG. 1. FIGS. 2, 3, and 4 show photon spectra for water, a water/alcohol mixture (Vodka), and melamine, respectively. The 2.223 MeV line is a clear signal that originates from the process described in (a) above and is common to all three targets. From the intensity of the 2.223 MeV line and information mentioned above, a measure of the density of hydrogen at the region of interest can be derived. The flux of the photon beam can be monitored by detectors above and below the container (not shown) or by other techniques available and demonstrated (e.g., by U.S. Pat. No. 7,372,262) on the determination of effective-Z and density in a three dimensional map of a container of material. Those skilled in the art will recognize different possibilities for the determination of photon intensity in a target and those are included herein as obvious extensions.

The spectra in FIGS. 2, 3, and 4 are accumulated by placing the targets as shown at location 12 in FIG. 1. That is, the targets are viewed both by the photon beam and by the detector.

In FIG. 2, in which water is the target, the 2.223 MeV line from neutron capture in hydrogen is clearly displayed. The NRF lines from 16O at 6.915.5 MeV and at 7.115.2 MeV are also observed along with their single and double escape peaks. The strong peak at 2.6145 MeV is background from the ThC in shielding and building material.

In FIG. 3, in which a mixture of alcohol and water (Vodka) is the target, the 2.2232 MeV line from neutron capture in hydrogen is clearly displayed. The NRF lines from 16O at 6.9155 MeV and at 7.1152 MeV are also observed along with their single and double escape peaks. The line at 4.438 from 12C and at 3.6839 MeV and 3.0891 MeV from 13C are observed. The background line from ThC at 2.6145 MeV is also observed.

In FIG. 4, in which melamine as the target, the hydrogen capture line at 2.2232 MeV is observed and along with the lines from the Carbon isotopes and the expected lines from nitrogen. These lines include: 12C at 4.438 MeV; 13C at 3.6839 MeV; 13C at 3.0891 MeV; 14N at 7.0272 MeV; 14N at 4.9142 MeV; 14N at 3.3783 MeV; 14N at 2.312 MeV. Also the ThC line is present as a background from building materials viewed by the detector at 2.6145 MeV.

Note that there are other lines that show up in the detector as well and these are displayed in FIGS. 2, 3, and 4. For the water target (FIG. 2), two additional lines appear; one at 6.9171 MeV and one at 7.1169 MeV. These follow from NRF on the 16O isotope. The fact that we see no other photon lines establishes clearly that the hydrogenous target is water (or an admixture of water and hydrogen peroxide). Were there an abundance of other elements in the primary voxel, the NRF lines from these elements would have been observed since NRF is almost ubiquitous in the periodic table.

The fusion of the data from the target in FIG. 3 clearly establishes the presence of hydrogen, carbon and oxygen. Analysis using the relative amounts calculated from these data as discussed above establishes that mixture is approximately what is expected from Vodka, a mixture of alcohol and water. The results of this analysis are presented in the chemical assaying section of this document.

As a point of clarification, the NRF gamma energies herein are the measured gamma energies, which include the Doppler shift due to the recoiling parent nucleus and thus are sometimes very slightly different (lower) that the energy from level designations.

Fusing the data in FIG. 4 as described above leads to the conclusion that the material is a combination approximately in the ratios expressed by the formula of melamine, C3H6N6. The results of this analysis are presented in the chemical assaying section of this document.

Bremsstrahlung as a photon source is used in one embodiment. It is preferred for many applications since the continuous nature of the spectrum covers all NRF states. A monochromatic photon source is another useful source; however, the photon source energetically will only be useful for NRF in the case the photon energy is resonant with a specific NRF state in a specific nucleus. This means that the monochromatic photon source might need to be tunable or provide multiple monochromatic lines to provide the possibility of covering NRF states from many nuclei. Each monochromatic source exceeding the ($\gamma$,n) threshold of deuterium (2.223 MeV) will also produce neutrons and characteristic 2.223 MeV photons upon capture of those neutrons. Each measurement using a monochromatic beam will have a characteristic ratio between the intensity of the NRF signal at that energy and the intensity of the 2.223 MeV gamma ray line. This ratio is proportional to the relative abundance of the isotope in question and the hydrogen in that measurement voxel.

In the exemplary system of FIG. 1, one detector system is shown. It is possible to use several such detector packages to provide simultaneously several independent views of different regions of a container.

Combined NRF and $^1$H(n,$\gamma$)D Assaying

When materials comprising hydrogen and other elements are irradiated with a beam having the properties above, the proportion of the NRF signal rates of individual elements and the neutron capture signal rates will be related to the proportion of the elements in the material, i.e. its chemistry or admixture.

Cross-Section Normalization

The rate at which the relevant signals are produced for a given beam intensity is defined by their reaction-cross sections, beam intensity at the voxel, detector efficiency, and attenuation of signals by intervening material. Effective use of the assaying technique involves accurate calibration for the signal production rate per elemental gram and beam charge. One such calibration technique is described below as an example and those skilled in the art will recognize other methods can be used and these are included herein as obvious.

Signal-rate determination for each material can be measured by controlling the following: (a) material quantity; (b) beam intensity at material location; (c) distance to radiation detector(s); (d) attenuation of intervening materials both inside and outside the cargo; (e) reaction cross sections involved in neutron production and thermalization, and NRF; (f) detector efficiencies; and (g) counting rate concerns including, among others, dead-time and saturation.

Chemical Assaying

Given the expected counts/gram for all lines corresponding to an element, any measurement can produce an estimate for the amount of mass of a given element present in the material. If all the estimates of all the masses of each element in a prepared library are combined to determine their relative mass fraction of the sample, an estimate for the relative chemical makeup of the sample is obtained. Using the experimental data of FIGS. 2, 3, and 4, estimates for the percent of the mass of specific elements are derived and presented in Table 1 below and these are compared with the average standard or "actual" values accepted for these materials. The samples used herein were contained in a 10 cm×10 cm×10 cm plastic "box." The counts from the elements in the material composing the box structure were subtracted experimentally from the data from each material plus box. No chemical analysis was made of the melamine or vodka to better determine the composition over and above the averages in the literature. Statistical counting uncertainties from the number of events accumulated dominate the disparities between the estimates and actual elemental compositions in Table 1.

The presence of a peak in the photon spectra unambiguously establishes the presence of a specific element. The differences between estimated and actual amounts are within the statistical uncertainties of the specific data set presented in FIGS. 2, 3, and 4 and can be improved by counting events with a longer exposure to the beam.

The data in Table 1 clearly demonstrate the usefulness of the neutron capture line from hydrogen combined with NRF in a fusion analysis to determine the chemical composition of hydrogenous materials and mixtures.

TABLE 1

| Material | % Hydrogen, estimated | % Hydrogen, actual | % Carbon, estimated | % Carbon, actual | % Oxygen, estimated | % Oxygen, actual | % Nitrogen, estimated | % Nitrogen, actual |
|---|---|---|---|---|---|---|---|---|
| Water | 14 | 11.1 | 0 | 0 | 85 | 88.8 | 1 | 0 |
| Melamine | 9 | 4.8 | 22 | 28.6 | 0 | 0 | 69 | 66.6 |
| Vodka | 11 | 11.9 | 15 | 20.1 | 74 | 67.2 | 0 | 0 |

The processes of the systems for analyzing the chemical makeup of a target hydrogenous material described above may be implemented in software, hardware, firmware, or any combination thereof. The processes are preferably implemented in one or more computer programs executing on a programmable computer including a processor, a storage medium readable by the processor (including, e.g., volatile and non-volatile memory and/or storage elements), and input and output devices. Each computer program can be a set of instructions (program code) in a code module resident in the random access memory of the computer. Until required by the computer, the set of instructions may be stored in another computer memory (e.g., in a hard disk drive, or in a removable memory such as an optical disk, external hard drive, memory card, or flash drive) or stored on another computer system and downloaded via the Internet or other network.

Having thus described several illustrative embodiments, it is to be appreciated that various alterations, modifications, and improvements will readily occur to those skilled in the art. Such alterations, modifications, and improvements are intended to form a part of this disclosure, and are intended to be within the spirit and scope of this disclosure. While some examples presented herein involve specific combinations of functions or structural elements, it should be understood that those functions and elements may be combined in other ways according to the present disclosure to accomplish the same or different objectives. In particular, acts, elements, and features discussed in connection with one embodiment are not intended to be excluded from similar or other roles in other embodiments. Additionally, elements and components described herein may be further divided into additional components or joined together to form fewer components for performing the same functions.

Accordingly, the foregoing description and attached drawings are by way of example only, and are not intended to be limiting.

What is claimed is:

1. A non-intrusive method of analyzing the chemical makeup of a target hydrogenous material sample in a voxel, the method comprising the steps of:
   (a) illuminating the target hydrogenous material sample in the voxel with a photon beam, wherein the energy of at least some photons in the photon beam is greater than 2.23 MeV;
   (b) measuring a number of 2.223 MeV photons produced by neutron capture and emitted from the target hydrogenous material sample in the voxel in a given measurement direction in a first energy range that contains the energy corresponding to neutron capture by hydrogen;
   (c) measuring a number of Nuclear Resonance Fluorescence (NRF) produced photons emitted from the target hydrogenous material sample the voxel in the given measurement direction in a second energy range;
   (d) determining the intensity of the 2.223 MeV photons produced by neutron capture in the target hydrogenous material sample in the voxel;
   (e) determining which isotopes are present in the target hydrogenous material sample in the voxel based on the number of NRF produced photons;
   (f) determining the intensities of the NRF produced photons;
   (g) determining the ratio of the abundances of the isotopes in the voxel from the intensities of the of the NRF produced photons;
   (h) determining the ratios of the hydrogen content in the voxel to the content of the isotopes of the target hydrogenous material sample in the voxel; and
   (i) determining the elemental composition of the target hydrogenous material sample in the voxel.

2. The method of claim 1, wherein the voxel is illuminated by a Bremsstrahlung photon beam.

3. The method of claim 1, wherein the voxel is illuminated by a monochromatic photon source.

4. The method of claim 3, wherein the monochromatic photon source comprises a tunable source, a source with more than one monochromatic line, or a source based on Compton scattering or focused Compton scattering.

5. The method of claim 1, wherein the photons in the photon beam illuminating the target hydrogenous material sample in the voxel are produced by (n,γ), (p,γ), or (α,γ) reactions.

6. The method of claim 1, wherein the photons illuminating the voxel are produced by a Compton or Thompson scattering from an energetic electron beam.

7. The method of claim 1, further comprising measuring the number of NRF produced photons emitted from the target hydrogenous material sample in the voxel in a second given measurement direction in the second energy range.

8. The method of claim 1, further comprising sweeping the photon beam across a container containing the target hydrogenous material sample to interrogate different regions of the container.

9. The method of claim 1, further comprising moving a container containing the target hydrogenous material sample through the photon beam to interrogate different regions of the container.

10. The method of claim 1, further comprising determining the absolute density of hydrogenous material in the target hydrogenous material sample using the ratio of the abundances of the isotopes in the voxel and data for photon beam attenuation.

11. The method of claim 10, wherein the data for photon beam attenuation is determined by estimation or measurement.

12. The method of claim 1, further comprising determining the absolute density of hydrogenous material in the target hydrogenous material sample using the ratio of the abundances of the isotopes in the voxel and data from look-up tables relating the intensity of the 2.223 MeV photons to the intensities of the NRF produced photons of selected combinations of possible and relevant compounds and mixtures established experimentally.

13. The method of claim 1, further comprising determining the absolute density of hydrogenous material in the target hydrogenous material sample using the ratio of the abundances of the isotopes in the voxel and data from theoretical calculations used to produce look-up tables or models relating the intensity of the 2.223 MeV photons to the intensities of the NRF produced photons of selected combinations of possible and relevant compounds and mixtures.

14. The method of claim 1, wherein the method is utilized to identify the presence and/or quantification of explosives, toxic substances, or general contraband.

15. The method of claim 1, wherein the method is utilized to identify materials in the flow of materials in a production line or transportation venue.

16. A non-intrusive system for analyzing the chemical makeup of a target hydrogenous material sample in a voxel, the system comprising:
  a photon source for illuminating the target hydrogenous material sample in the voxel with a photon beam, wherein the energy of at least some photons in the photon beam is greater than 2.23 MeV;
  one or more detectors for (i) detecting a number of 2.223 MeV photons produced by neutron capture and emitted from the target hydrogenous material sample in the voxel in a given measurement direction in a first energy range that contains the energy corresponding to neutron capture by hydrogen, and (ii) detecting a number of Nuclear Resonance Fluorescence (NRF) produced photons emitted from the target hydrogenous material sample the voxel in the given measurement direction in a second energy range; and
  a computer system, comprising at least one processor, memory associated with the at least one processor, and a program supported in the memory, the program containing a plurality of instructions which, when executed by the at least one processor, cause the at least one processor, in response to data received from the one or more detectors, to:
  (a) determine the intensity of the 2.223 MeV photons produced by neutron capture in the target hydrogenous material sample the voxel;
  (b) determine which isotopes are present in the target hydrogenous material sample in the voxel based on the number of NRF produced photons;
  (c) determine the intensities of the NRF produced photons;
  (d) determine the ratio of the abundances of the isotopes in the voxel from the intensities of the of the NRF produced photons;
  (e) determine the ratios of the hydrogen content in the voxel to the content of the isotopes of the target hydrogenous material sample in the voxel; and
  (f) determine the elemental composition of the target hydrogenous material sample in the voxel.

17. The system of claim 16, wherein the one or more detectors include a spectroscopic x-ray detector.

18. The system of claim 16, wherein the photon beam is a Bremsstrahlung photon beam.

19. The system of claim 16, wherein the photon source is a monochromatic photon source.

20. The system of claim 19, wherein the monochromatic photon source comprises a tunable source, a source with more than one monochromatic line, or a source based on Compton scattering or focused Compton scattering.

21. The system of claim 16, wherein the photons in the photon beam illuminating the target hydrogenous material sample in the voxel are produced by $(n,\gamma)$, $(p,\gamma)$, or $(\alpha,\gamma)$ reactions.

22. The system of claim 16, wherein the photons illuminating the voxel are produced by a Compton or Thompson scattering from an energetic electron beam.

23. The system of claim 16, wherein the one or more detectors further detect the number of NRF produced photons emitted from the target hydrogenous material sample in the voxel in a second given measurement direction in the second energy range.

24. The system of claim 16, wherein the photon source sweeps the photon beam across a container containing the target hydrogenous material sample to interrogate different regions of the container.

25. The system of claim 16, further comprising a mechanism for moving a container containing the target hydrogenous material sample through the photon beam to interrogate different regions of the container.

26. The system of claim 16, wherein the computer system further determines the absolute density of hydrogenous material in the target hydrogenous material sample using the ratio of the abundances of the isotopes in the voxel and data for photon beam attenuation.

27. The system of claim 26, wherein the data for photon beam attenuation is determined by estimation or measurement.

28. The system of claim 16, wherein the computer system further determines the absolute density of hydrogenous material in the target hydrogenous material sample using the ratio of the abundances of the isotopes in the voxel and data from look-up tables relating the intensity of the 2.223 MeV photons to the intensities of the NRF produced photons of selected combinations of possible and relevant compounds and mixtures established experimentally.

29. The system of claim 16, wherein the computer system further determines the absolute density of hydrogenous material in the target hydrogenous material sample using the ratio of the abundances of the isotopes in the voxel and data from theoretical calculations used to produce look-up tables or models relating the intensity of the 2.223 MeV photons to the intensities of the NRF produced photons of selected combinations of possible and relevant compounds and mixtures.

30. The system of claim 16, wherein the system is configured to identify the presence and/or quantification of explosives, toxic substances, or general contraband.

31. The system of claim 16, wherein the system is configured to identify materials in the flow of materials in a production line or transportation venue.

* * * * *